US007996508B2

(12) United States Patent
Masciantonio et al.

(10) Patent No.: US 7,996,508 B2
(45) Date of Patent: Aug. 9, 2011

(54) SYSTEM AND METHOD FOR LOCATING PROVIDERS OVER THE INTERNET ON SHORT NOTICE

(75) Inventors: Angelo Masciantonio, Radnor, PA (US); Eliot Heher, Wellesley, MA (US); Peter J. Bohn, Ardmore, PA (US)

(73) Assignee: Highway to Health, Inc., Radnor, PA (US)

( * ) Notice: Subject to any disclaimer, the term of this patent is extended or adjusted under 35 U.S.C. 154(b) by 1023 days.

(21) Appl. No.: 11/599,252

(22) Filed: Nov. 15, 2006

(65) Prior Publication Data
US 2007/0067391 A1    Mar. 22, 2007

Related U.S. Application Data

(62) Division of application No. 09/703,612, filed on Nov. 2, 2000, now Pat. No. 7,260,603.

(60) Provisional application No. 60/163,065, filed on Nov. 2, 1999.

(51) Int. Cl.
    *G06F 15/16*    (2006.01)
(52) U.S. Cl. ........................................... 709/223; 705/2
(58) Field of Classification Search .................. 709/203, 709/204, 205, 217, 223, 224; 705/1, 2, 3, 705/5
    See application file for complete search history.

(56) References Cited

U.S. PATENT DOCUMENTS

| 5,065,315 | A | 11/1991 | Garcia | 364/413.01 |
| 5,072,383 | A | 12/1991 | Brimm et al. | 364/413.02 |
| 5,077,666 | A | 12/1991 | Brimm et al. | 364/413.02 |
| 5,124,912 | A | 6/1992 | Hotaling et al. | 364/401 |
| 5,197,000 | A | 3/1993 | Vincent | 364/401 |
| 5,301,105 | A | 4/1994 | Cummings, Jr. | 364/401 |
| 5,960,406 | A | 9/1999 | Rasansky et al. | 705/9 |
| 6,047,274 | A | 4/2000 | Johnson et al. | 705/412 |
| 6,091,956 | A | 7/2000 | Hollenberg | 455/456.5 |
| 6,345,260 | B1 | 2/2002 | Cummings et al. | 705/8 |
| 6,526,335 | B1 | 2/2003 | Treyz et al. | 701/1 |
| 6,581,040 | B1 | 6/2003 | Wright et al. | 705/8 |
| 6,587,838 | B1 | 7/2003 | Esposito et al. | 705/28 |
| 6,681,327 | B1 * | 1/2004 | Jardin | 713/153 |
| 6,973,434 | B2 | 12/2005 | Miller | 705/2 |

OTHER PUBLICATIONS

TEBCOMP Medical Development:CliniMed Software (1997).
D. Berlind, "PC Week", Jan. 8, 1996.
Starfish.com: Sidekick 98 (1998).
Annex to Form PCT/ISA/206 Communication Relating to the Results of the Partial International Search dated Feb. 11, 2000.

(Continued)

*Primary Examiner* — William C Vaughn, Jr.
*Assistant Examiner* — Scott Christensen (57) ABSTRACT

A system for allowing members or prospective members to simultaneously contact multiple providers to secure an appointment on short notice. The system also enables the provider to view or obtain requests for appointments from members who the provider may not have previously met and/or served. The system further enables a facilitator 304 to monitor the communication exchanges between members and providers and to intervene directly if needed. The system includes a web application, a provider network, facilitator, a database server, a web server, and a database. The web application includes a web site that facilitates interaction between members, providers, the facilitator and the system. The web site also includes a list of common medical terms, phrases, and pharmaceuticals that are cross-referenced in multiple languages. The provider network processes information provided by users of the system and the database stores information processed in the system.

13 Claims, 5 Drawing Sheets

System 300

OTHER PUBLICATIONS

"MultiLingual Glossary of Technical and Popular Medical Terms in Nine European Languages", Heymans Institute of Pharmacology, University of Gent, Dec. 1995.

Arabshian et al. A SIP-based Medical Event Monitoring System, Jun. 2003, IEEE, pp. 66-70.

* cited by examiner

Fig. 1

Application Layer / Layer 5
202

Transport Layer / Layer 4
204

Internet Layer / Layer 3
206

Network Interface Layer / Layer 2
208

Physical Layer / Layer 1
210

TCP/IP Layering Model

Fig. 4  Home Page

Fig. 5

SYSTEM AND METHOD FOR LOCATING PROVIDERS OVER THE INTERNET ON SHORT NOTICE

The present application is a Divisional of U.S. Patent Application No. 90/703,612 filed Nov. 2, 2000 now U.S. Pat. No. 7,260,603 and claims the benefit of U.S. Provisional Application No. 60/163,065 filed on Nov. 2, 1999, which are both hereby incorporated by reference.

FIELD OF THE INVENTION

The present invention relates to a method for locating information on the Internet, and more particularly, to a system and method for locating providers and/or products on short notice.

BACKGROUND OF THE INVENTION

Advances in computer processing power and network communications have made information from a wide variety of sources available to users on computer networks. Computer networking allows network computer users to share information, software applications and hardware devices and internetworking enables a set of physical networks to be connected into a single network such as the Internet. Today, computers connected to the Internet have almost instant access to information stored in relatively distant regions. Moreover, computers connected to networks other than the Internet also have access to information stored on those networks. The World Wide Web (Web), a hypermedia system used on the Internet, enables hypertext linking, whereby documents automatically reference or link other documents located on connected computer networks around the world. Thus, users connected to the Internet have almost instant access to information stored in relatively distant regions.

A page of information on the Web may include references to other Web pages and may include a broad range of multimedia data including textual, graphical, audio, and animation information. Currently, Internet users retrieve information from the Internet, through the Web, by 'visiting' a web site on a computer that is connected to the Internet.

The web site is, in general terms, a server application that displays information stored on a network server computer. The web site accepts connections from client programs, such as Internet browser applications. Browser applications, such as Microsoft Explorer™ or Netscape Internet Browser™, allow Internet users to access information displayed on the web site. Most browser applications display information on computer screens and permit a user to navigate through the Web using a mouse. Like other network applications, Web browsing uses the client-server paradigm where state is maintained as an adjunct to the HTTP protocol. When given the Uniform Resource Locator (URL) of a document, the browser application becomes a client and it contacts a server application specified in the URL to request the document. After receiving the document from the server application, the browser application displays the document for the user. When the browser application interacts with the server application, the two applications follow the Hyper-Text Transport Protocol (HTTP). HTTP allows the browser application to request a specific article, which the server application then returns. To ensure that browser applications and server applications inter-operate unambiguously, HTTP defines the exact format for requests sent from the browser application to the server application as well as the format of replies that the server application returns.

As the number of physical networks connected to the Internet continues to grow, so too will the number of web sites that are accessible to Internet users and so too will commercial and other activity on the Internet. Providers of products and/or services use the Internet to offer better and faster services to members. For example, providers of health insurance enable their members to use the Internet to find medical providers within a specified geography area. Upon finding the desired medical provider, the member may sign up or set an appointment with the provider by traditional means, such as a telephone call, or through the Internet. Most medical providers schedule appointments in advance. Therefore, this method of finding medical providers is adequate for normal appointment scheduling. However, members who need to make an appointment on short notice may have a harder time finding a provider using this method. When the member obtains a list of providers within a specified area, the member has no way of determining which providers have opening slots in their schedule. The problem of finding a provider on short notice is even more acute for members who are outside of their normal provider network or in a distant and/or unfamiliar city. Moreover, for members travelling internationally, there may be communication problems with providers who speak different languages.

Additionally, if a provider schedule opens up, for example through cancellation, the provider has no way of filling an appointment slot by finding members who are seeking appointments on short notice. What is needed, therefore, is a system and method for enabling members and providers to obtain appointments on short notice. The system must also facilitate communications between members and providers speaking different languages.

SUMMARY OF THE INVENTION

The present invention relates to a system and method for quickly and conveniently using the Internet to locate information on electronically-linked groups of providers. The system includes a global database of on-line professionals and uses e-mail, transmissions on the Web, and/or fax communications to simultaneously contact multiple providers to schedule an appointment for a member.

It is an object of the invention to provide a system for allowing members or prospective members to simultaneously contact multiple providers to secure an appointment on short notice. The system also enables the provider to view or obtain and/or served.

It is another object of the invention to enable a facilitator to monitor communications exchanges between members and providers and to intervene directly if needed. The facilitator provides the means for the exchange to occur between the provider and the member and maintains information in the system.

It is another object of the invention to include a web application, a provider network, a facilitator, a database server, a web server, and a database. The web application includes a web site that facilitates system interaction. The provider network processes information provided by users of the system and the database stores information processed in the system. The database server maintains the database, as well as supplementary information that is necessary to run the system.

It is another object of the invention to allow the member to specify a geographic location and other required criteria.

It is another object of the invention for the provider network to provide, upon request from the member, a list of providers that meet the specified criteria, identify each provider's proximity to the member's location and to provide biographical information of each provider.

It is another object of the invention to allow the member to select multiple providers from the list and submit the list of selected providers to the system.

It is another object of the invention for the provider network to generate a notification for each selected provider in order for the provider to respond to the requested appointment.

It is another object of the invention to communicate providers' responses to the member so that the member can confirm the appointment.

It is an object of the present invention to provide different types of access with different rates to the system to members based on members' travelling frequency. The travelling member may purchase access to the system through appropriate agents, such as travel agents, hotels, and rental car companies and through a corresponding on-line web site. Additionally, the travelling member may purchase access in advance at a discount instead of at a premium rate on an as-needed basis during a trip.

It is another object of the system to allow members and participating providers to access the web site from a variety of platforms, browsers, and modems. Moreover, members and/or participating providers without access to computers or the web may access the system through a telephone calling service.

It is another object of the invention to provide different types of privileges for accessing data and different modes of operation and associated functionality to different levels of members. Members at all levels may access the system through an on-line web site, e-mail, telephone calls, faxes and/or other means.

It is another object of the invention to provide a system for translating commonly used medical phrases and popular prescription drugs between multiple languages. The system may also translate prescription drugs into appropriate dosage and brand names as they may appear in different locations.

Additional features and advantages of the invention will be set forth in the description that follows, and in part will be apparent from the description, or may be learned by practice of the invention. The objectives and advantages of the invention will be realized and attained by the system particularly pointed out in the written description and claims hereof as well as the appended drawings.

To achieve these and other advantages and in accordance with the purpose of the invention, as embodied and broadly described, the present invention provides a system for allowing users to simultaneously contact multiple providers to secure an appointment on short notice, the system comprising: a facilitator that sets up, mediates, and monitors communications between the providers and the users and intervenes directly if needed; a web application that includes a web site for facilitating interaction with the system; a provider network for processing information provided by users of the system; and a storage device for storing information processed by the system.

The invention also provides a method for enabling a user to simultaneously contact multiple providers to secure an appointment on short notice, the method comprising the steps of: entering, by the user, at least one required criterion on a system web site; determining, by the system, each provider within a specified area that meets the required criterion and identifying each provider's proximity to the user's location; providing, by the system, a list of providers to the user; selecting, by the user, multiple providers from the list and submitting the selected multiple providers to the system; notifying, by the system, the selected providers; responding to the notification by each selected provider; displaying to the user, by the system, the responses from each selected provider; confirming, by the user, one response with one selected provider; and notifying, by the system, those providers whose responses were not accepted by the user.

The invention also provides a method for enabling a facilitator to mediate communication exchanges between users and providers of a system that allows the users to simultaneously contact multiple providers to secure an appointment on short notice, the method comprising the steps of: allowing the facilitator to view exchanges and histories of exchanges between users and providers; contacting the facilitator, by a user, to specify at least one required criterion for selecting a provider; determining, by the facilitator, each provider within a specified area that meets the at least one required criterion, identifying each provider's proximity to the user's location and providing a list of providers to the user; selecting, by the user, multiple providers from the list and submitting the selected multiple providers to the facilitator; notifying, by the facilitator, the selected multiple providers; responding, by the provider, to the notification; communicating, by the facilitator, the responses to the user; confirming, by the user, one response with one selected provider; and notifying, by the facilitator, those providers whose responses were not accepted by the user.

BRIEF DESCRIPTION OF THE DRAWINGS

The accompanying drawings, which are included to provide a further understanding of the invention and are incorporated in and constitute a part of this specification, illustrate embodiments of the invention that together with the description serve to explain the principles of the invention.

In the drawings.

DESCRIPTION OF THE PREFERRED EMBODIMENTS

Reference will now be made in detail to the preferred embodiments of the present invention, examples of which are illustrated in the accompanying drawings. The present invention described below extends the functionality of the inventive system and method for locating providers over the Internet on short notice.

Figure 1:
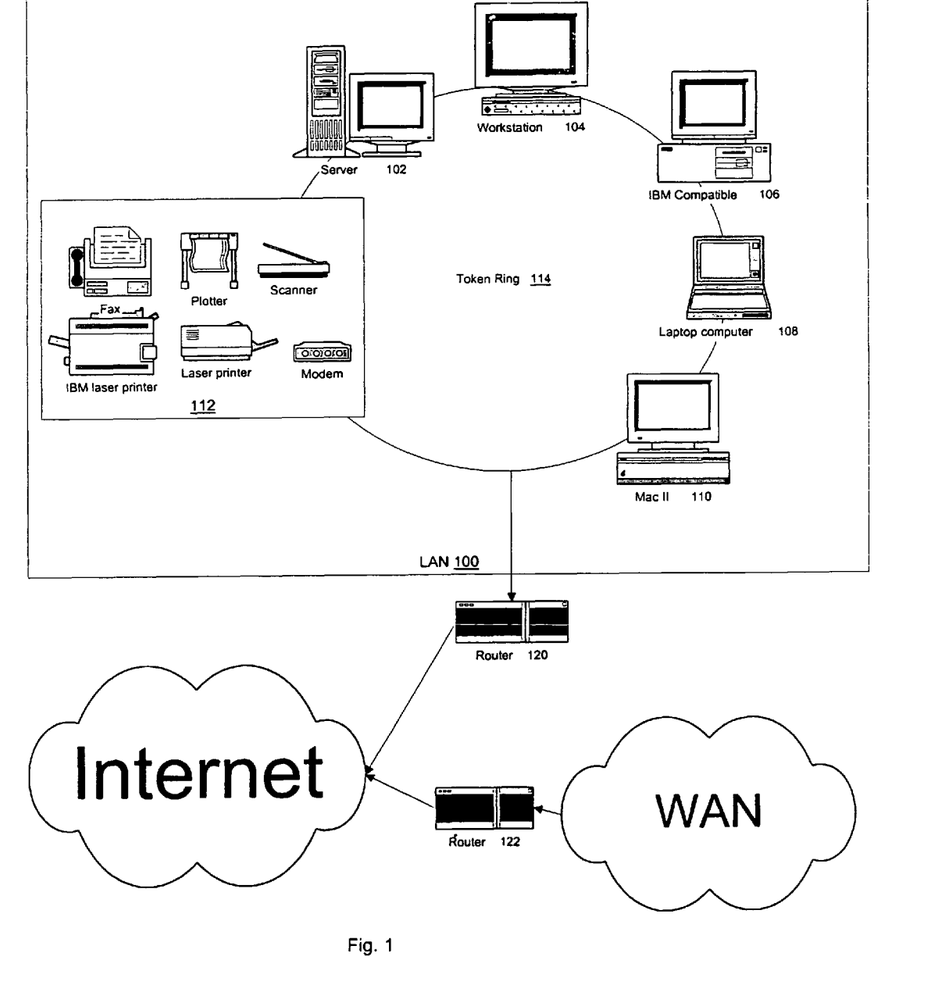
FIG. 1 illustrates a computer network in which the inventive information system may be incorporated.

FIG. 1 is an example of a local area network (LAN) 100 that is configured to utilize a non-repudiation protocol. LAN 100 comprises a server 102, four computer systems 104-110, and peripherals, such as printers and other devices 112, that may be shared by components on LAN 100. Computer systems 104-110 may serve as clients for server 102 and/or as clients and/or servers for each other and/or for other components connected to LAN 100. Components on LAN 100 are preferably connected together by cable media, for example copper or fiber-optic cable and the network topology may be a token ring topology 114. It should be apparent to those of ordinary skill in the art that other media, for example, wireless media, such as optical and radio frequency, may also connect LAN 100 components. It should also be apparent that other network topologies, such as Ethernet, may be used.

Data may be transferred between components on LAN 100 in packets, i.e., blocks of data that are individually transmitted over LAN 100. Routers 120, 122 create an expanded network by connecting LAN 100 to other computer networks, such as the Internet, other LANs or Wide Area Networks (WAN). Routers are hardware devices that may include a conventional processor, memory, and separate I/O interface for each network to which it connects. Hence, components on the expanded network may share information and services with each other. In order for communications to occur between components of physically connected networks, all components on the expanded network and the routers that connect them must adhere to a standard protocol. Computer networks connected to the Internet and to other networks typically use TCP/IP Layering Model Protocol. It should be noted that other internetworking protocols may be used.

Figure 2:
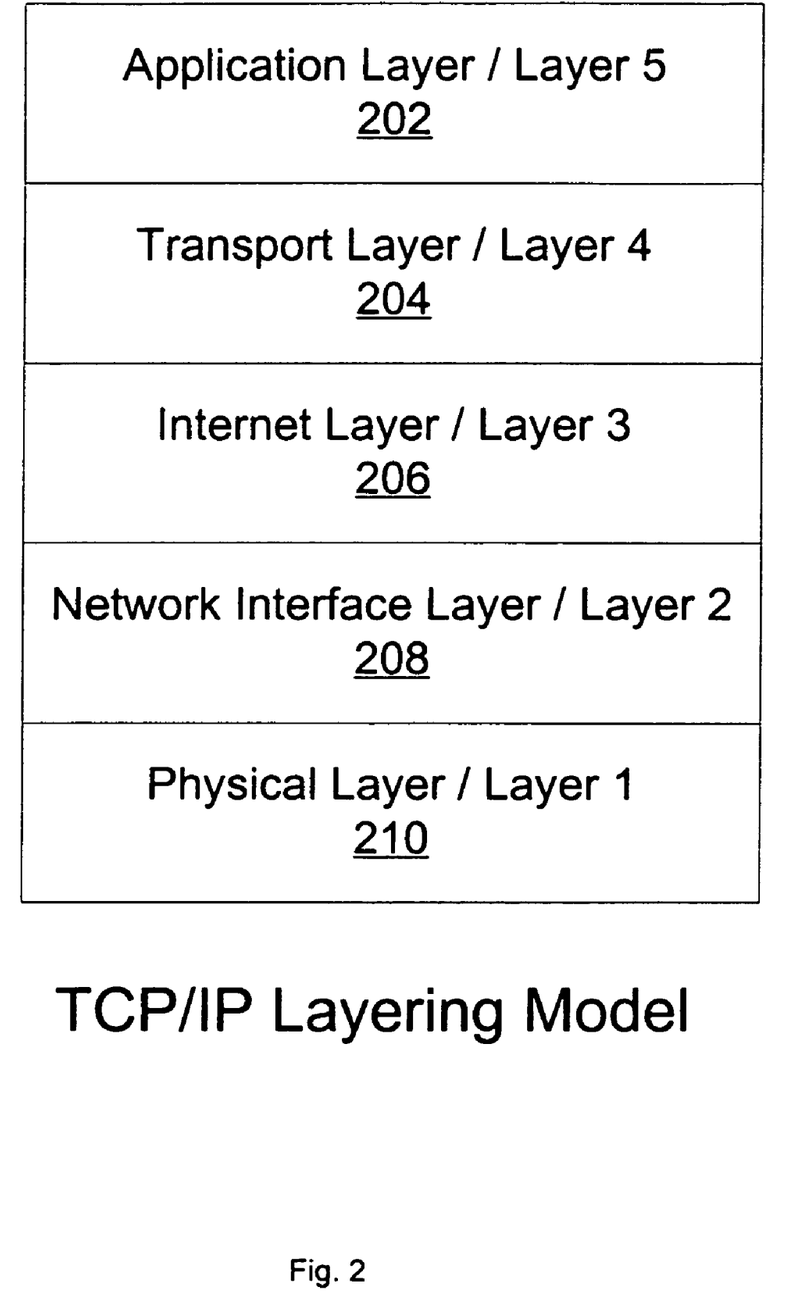
FIG. 2 illustrates the TCP/IP Layering Model Protocol used during communications between components on the computer network.

As illustrated in FIG. 2, TCP/IP Layering Model comprises an application layer or (Layer 5) 202, a transport layer or (Layer 4) 204, an Internet layer or (Layer 3) 206, a network interface layer or (Layer 2) 208, and a physical layer or (Layer 1) 210. Application layer protocols 202 specify how each software application connected to the network uses the network. Transport layer protocols 204 specify how to ensure reliable transfer among complex protocols. Internet layer protocols 206 specify the format of packets sent across the network as well as mechanisms used to forward packets from a computer through one or more routers to a final destination. Network interface layer protocols 208 specify how to organize data into frames and how a computer transmits frames over the network. Physical layer protocols 210 correspond to the basic network hardware. By using TCP/IP Layering model protocols, any component connected to the network can communicate with any other component connected directly or indirectly to one of the attached networks.

Figure 3:
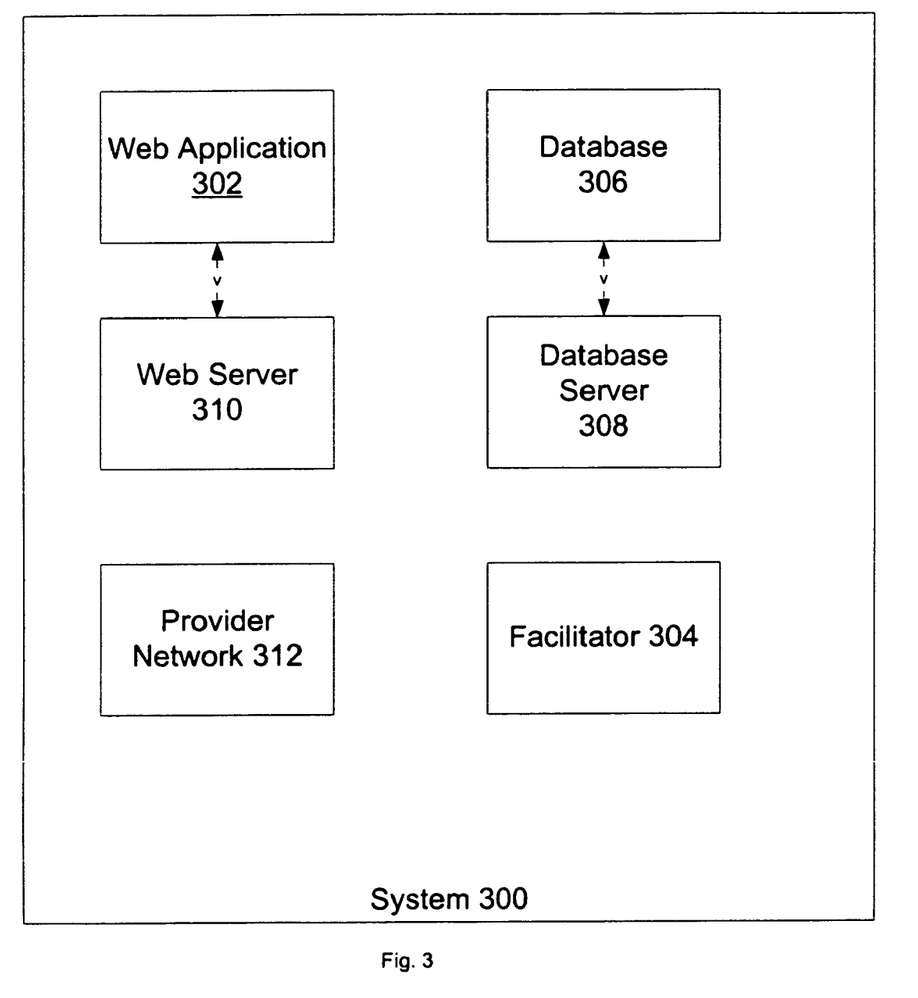
FIG. 3 illustrates an inventive web-enabled information system for allowing remote access to an appointment scheduling system.

FIG. 3 illustrates to a system 300 for allowing members or prospective members to simultaneously contact multiple providers to secure an appointment on short notice. System 300 also enables the provider to view or obtain requests for appointments from members who the provider may not have previously met and/or served. System 300 further enables a facilitator 304 to monitor the communication exchanges between members and providers and to intervene directly if needed. Facilitator 304 is a body that sets up and mediates all communications between members and providers. Facilitator 304 provides the means for the exchange to occur between the provider and the member and maintains information in system 300.

System 300 includes a web application 302, a provider network 312, facilitator 304, a database server 308, a web server 310, and a database 306. The web application 302 includes a web site that facilitates interaction between members, providers, facilitator 304 and system 300. The web site also includes a list of common medical terms, phrases, and pharmaceuticals that are cross-referenced in multiple languages. Pharmaceuticals are often manufactured under different names in different countries. Thus, the web site facilitates communications between members who are travelling internationally and providers in international countries. System 300 also facilitates communications by cross-referencing common terms and phrases. For example, if a member who does not speak Japanese has a toothache in Japan, the member may find the Japanese word for toothache on the web site in order to communicate with a provider and obtain care in Japan. Provider network 312 processes information provided by users of system 300 and database 306 stores information processed in system 300. Database 306 includes information about members, providers, insurance products and medical cases processed by system 300. Database server 308 maintains database 306 as well as supplemental information, which is necessary to run the information system. An example of a database server used in the inventive system is a Windows NT™ Server system running Oracle Workgroup Server™ in a client-server mode of operation. The web server converts all HTTP-based requests addressed to the system to native commands for processing by the database server and uses information gathered from the server to dynamically generate HTML pages in response to the requests. The Web application may be based on a web application software, such as Oracle Web Application Server™ software, currently installed on the same server computer as the database server or other computer on the network.

System 300 provides different types of access with different rates to members based on predetermined criteria, such as the members' travelling frequency. The travelling member may purchase access to system 300 through appropriate agents, such as travel agents, hotels, and rental car companies and/or through a corresponding on-line web site. Additionally, the travelling member may purchase access in advance at a discount instead of at a premium rate on an as-needed basis during a trip. System 300 also provides different types of privileges for accessing data and different modes of operations and associated functionality to different levels of members. Members at all levels may access system 300 through an on-line web site, e-mail, telephone calls, faxes and/or other means.

Specifically in a preferred embodiment of the invention, when a member visits the web site, the member specifies a geographic location and other required criteria. For example, the member may specify what kind of specialist is required, the language that the member speaks, the date and time or range of times when an appointment is desired, or if the first available appointment is desired. System 300 uses a geo-locator tool to determine the longitude and latitude of each provider within a specified area. Provider network 312 provides a list of providers that meet the specified criteria and identifies each provider's proximity to the member's location. Additionally, provider network 312 provides biographical information of each provider. For example, provider network 312 provides the school(s) attended by each provider and professional accreditation and affiliation(s) of each provider. As is obvious to one skilled in the art, other information may be displayed, and are within the scope of the present invention.

Upon viewing the list of providers, including the location and biographical information for each provider, the member may select multiple providers from the list. The member submits a list of selected providers to system 300 and provider network 312 uses unique identifiers assigned to each provider to generate an e-mail message or a fax notification for each provider. As is apparent to one of ordinary skill in the art, other notification means may be used, and are within the scope of the present invention. System 300 transmits the notification to the provider's office. Upon receipt of the notification, the provider may visit the web site, enter an authentication code and respond to the requested appointment. For example, the provider may visit the web site, enter a user name and password, and offer an appointment for a specific date and time. Alternatively, the provider may fax a response to facilitator 304. The responses from the providers are stored in database 306 and at a predetermined time, provider network 312 collates the responses and forwards them to the member. Alternatively, provider network 312 collates the responses and at a later time when the member logs into the system with a username and password, the member is shown a list of all responses. Alternatively, provider network 312 may forward responses, through e-mail messages to the member, as the responses are entered into the system. The member may confirm a response from a provider directly with the provider's office or respond via clicking on a button, in system 300, that is associated with the provider's response. Those providers' whose responses are not accepted by the member are notified by system 300. If the member accepts a response through system 300, the provider may confirm the appointment through the system, by sending a message to the member.

In a preferred embodiment of the invention, facilitator 304 is interested in ensuring that requests are answered in a timely fashion. Thus, facilitator 304 is allowed to view exchanges and histories of exchanges between members and providers. Specifically, facilitator, 304 checks that each request has been processed within a certain period of time. If a request has not been processed, an alert status is issued to a monitoring group and a member of the monitoring group directly intervenes by calling providers to set up an appointment or by calling the member and asking if the member wants to choose another set of providers.

In an alternate embodiment, the member seeking an appointment contacts facilitator 304 directly. The member specifies the requirements for the specialist. Facilitator 304 uses system 300 to obtain a list of providers that meet the specified criteria and identifies each provider's proximity to the member's location. The member selects providers from the list and facilitator 304 sends a notification to each selected provider. Upon receipt of the notification, the provider may visit the web site or contact facilitator 304 to respond to the requested appointment. Facilitator 304 communicates the response to the member. The member may confirm a response from a provider directly with the provider's office or through facilitator 304. Facilitator 304 notifies those providers whose responses are not accepted by the member.

Additionally, if appointment times become available for a provider, due to cancellation, for example, the provider may log into system 300 and enter the available appointment times. Thereafter, when a member logs into system 300, the member may view all providers with appointments available at a desired time. The member is also shown a list of providers without open appointments. The member selects a list of providers, with or without open appointments, and submits the list to system 300. It should be noted that it is more likely that the member will select providers with open appointment slots than those without. Provider network 312 generates a notification for each selected provider. System 300 transmits the notification to the provider's office. Upon receipt of the notification, the provider responds to the requested appointment. The responses from the providers are presented to the member. The member confirms a response from a provider and those providers' whose responses are not accepted by the member are notified by system 300. If the member accepts a response through system 300, the provider may confirm the appointment through system 300, by sending a message to the member.

Alternatively, when the provider enters available appointment times, system 300 may provide a list of members seeking appointments at that time. The provider may then contact the member to schedule an appointment time.

Figure 4:
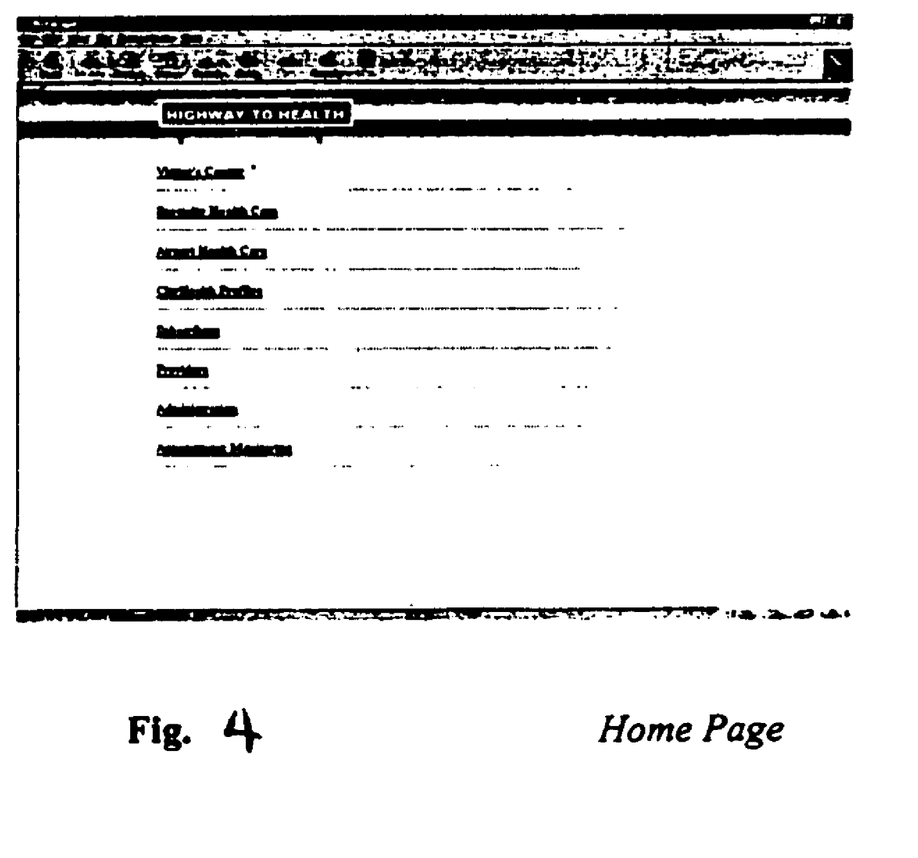
FIG. 4 illustrates a main system menu which contains hyperlinks to other menus in the information system.

FIG. 4 illustrates a main menu for the inventive system. System is accessible through the main page on the Web by typing associated Uniform Resource Locator (URL). The URL connects a client browser to a host system through a default port of the web server. If confidential information is being transmitted between the client browser and the host system, a different port may be used so that the session may be held over secure Internet protocol, such as SSL. Upon accessing the main page, the users may navigate through system 300 by using hyper links to other pages. Active components of the information system are organized around a highway metaphor, whereby signs lead to corresponding functionality according to the steps of the entire process. Members may interact with system 300 by browsing for information stored in the system, by entering new information into the system and by updating information in the system.

Prior to using system 300, the provider must register with the system. Registration is a multiple step procedure, which requires the provider to first register a practice and then to register individual providers in the medical practice. Registration of the practice enables forward registration of practices for future partnerships. Information supplied during registration of the practice includes basic information about the practice, address information and optional registration of multiple offices. Facilitator 304 performs activation of the registered practice after predefined contract agreements are ratified. Practices may also be set up non-electronically by the facilitator 304.

An individual provider web page is used for registration of individual providers within system 300. The individual provider web page provides a detailed form for individual provider registration and includes professional information, office information and contact information. Facilitator 304 performs activation of registered providers after checking the correctness of the information supplied in the individual providers web page and after validating relationships for providers within the respective practice. Individual providers may also register non-electronically. As is obvious, all registration information may be updated through system 300 at a later date.

Figure 5:
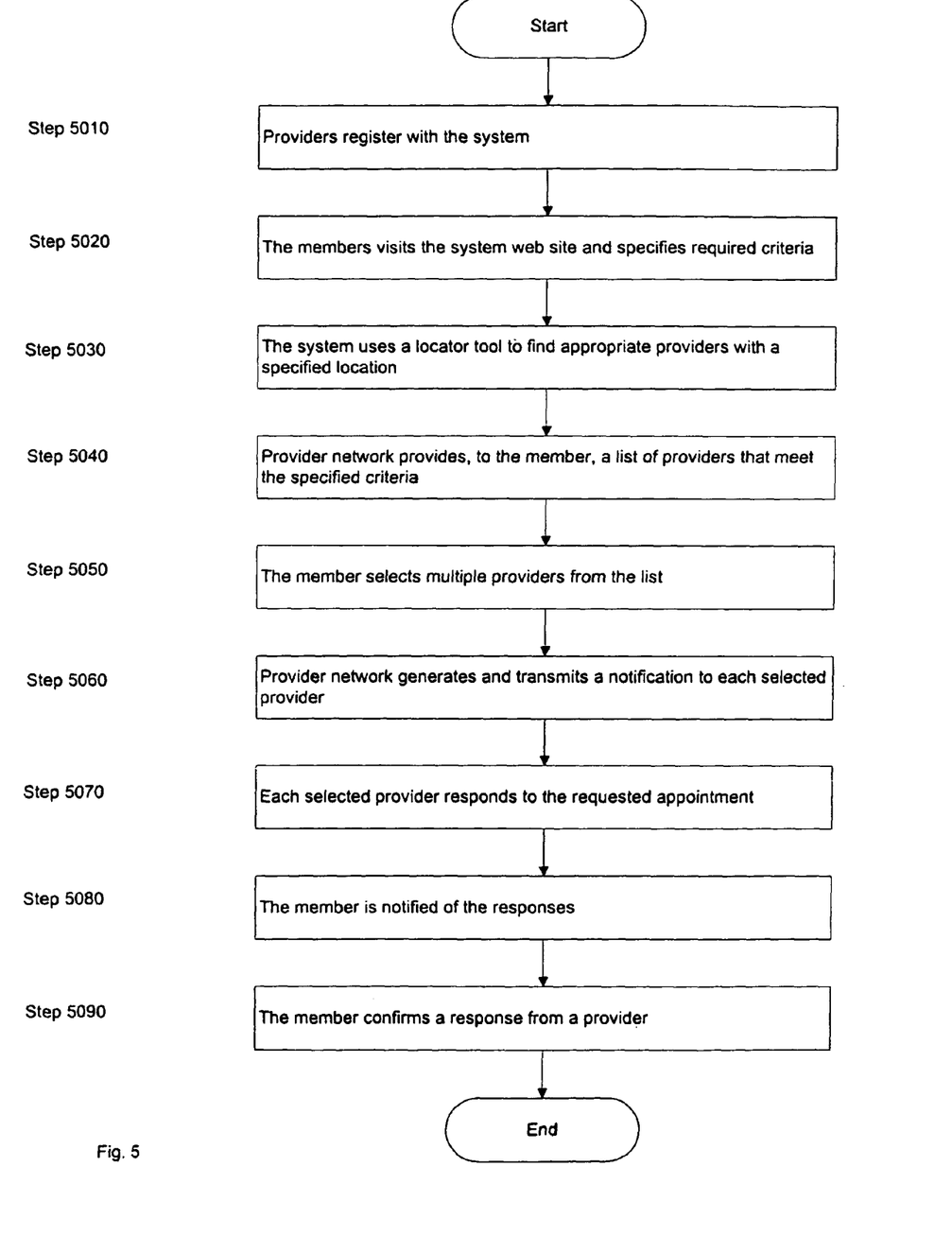
FIG. 5 illustrates the steps implemented by the inventive system.

FIG. 5 illustrates the steps implemented in the present invention. In Step 5010, the providers register with system 300. In Step 5020, a member visits the web site and specifies a geographic location and other required criteria. In Step 5030, system 300 uses a geo-locator tool to determine the longitude and latitude of each provider within a specified location. In Step 5040, provider network 312 provides a list of providers that meet specified criteria and identifies each provider's proximity to the member's location. In Step 5050, upon viewing the list of providers, the member may select multiple providers from the list and submit the list of selected providers to system 300. In Step 5060, provider network 312 uses unique identifiers assigned to each provider to generate a notification for each provider and system 300 transmits the notification to the provider's office. In Step 5070, upon receipt of the notification, the provider responds to the requested appointment. In Step 5080, the member is notified of the responses. In Step 5090, the member may confirm a response from a provider and those providers whose responses are not accepted by the member are notified.

The foregoing description has been directed to specific embodiments of this invention. It will be apparent, however, that other variations and modifications may be made to the described embodiments, with the attainment of some or all of their advantages. Therefore, it is the object of the appended claims to cover all such variations and modifications as come within the true spirit and scope of the invention.

What is claimed is:

1. A system for allowing users to simultaneously contact multiple providers to secure an appointment on short notice, the system comprising:
   a facilitator that sets up and mediates a communication including a request for an appointment generated from a user and a response generated from at least one provider in response to the request,
      wherein the facilitator receives the communication and generates a real-time list of at least one provider that meets criteria in the user's communication, presents the list to the user for selecting at least one provider, and transmits the request for appointment to the selected at least one provider whose response may be returned to the facilitator;
   a monitor that monitors the communication, including checking that the response is generated within a predefined time period and intervenes directly if the response is not generated in the predefined time period;
   a web application that includes a web site for facilitating interaction with the system, the web site including a translator having at least a medical term and phrase list translated in a plurality of languages of a plurality of countries and a pharmaceutical drug list compiled in each of the plurality of countries, the pharmaceutical drug list including at least formulation information and brand name information of a plurality of pharmaceutical drugs as manufactured or distributed in the plurality of countries, the translator providing cross-referencing between the plurality of countries of the at least formulation and brand name information of the plurality of pharmaceutical drugs,
      wherein the medical term and phrase list enables communication between users and providers who speak different languages;
   a provider network for processing information provided by users of the system; and
   a storage device for storing information processed by the system including the medical term and phrase list.

2. The system of claim 1, wherein each provider is allowed to view and obtain requests for appointments from new users.

3. The system of claim 1, wherein users are both members who have previously registered with the system and prospective members of the system.

4. The system of claim 1, wherein the storage device includes a database for storing information and a data server for maintaining the database and information, which is necessary to run the system.

5. The system of claim 1, wherein the web application includes a web server for converting all hypertext based requests to native commands for processing by components of the storage device and for dynamically generating HTML pages in response to the requests.

6. The system of claim 1, wherein the system provides different types of access and privileges to different users based on at least one predetermined criterion.

7. The system of claim 6, wherein users may purchase access to the system through appropriate agents.

8. The system of claim 6, wherein users may purchase access to the system through the web site.

9. The system of claim 1, wherein users may access the system through on-line means.

10. The system of claim 1, wherein users may access the system through off-line means.

11. The system of claim 1, wherein prior to using the system, providers must register a practice and the individual providers in the practice and the facilitator activates the registration after predefined contract agreements are ratified.

12. The system of claim 11, wherein providers may register practices for future partnerships.

13. The system of claim 1, wherein the facilitator intervenes directly by contacting at least one of the providers and users to secure the appointment.

* * * * *